United States Patent [19]

Seko et al.

[11] 4,230,882
[45] Oct. 28, 1980

[54] PROCESS FOR THE PRODUCTION OF A HIGH PURITY TEREPHTHALIC ACID

[75] Inventors: Maomi Seko; Tetsuya Miyake, both of Tokyo; Hiroshi Takeuchi; Masatoshi Tanouchi, both of Nobeoka, all of Japan

[73] Assignee: Asahi Kasei Kogyo Kabushiki Kaisha, Osaka, Japan

[21] Appl. No.: 907,773

[22] Filed: May 19, 1978

[51] Int. Cl.$^2$ ............................................. C07C 51/33
[52] U.S. Cl. ................................................... 562/416
[58] Field of Search ................................ 562/416, 417

[56] References Cited

U.S. PATENT DOCUMENTS

| 3,240,803 | 3/1966 | Thompson | 562/417 |
| 3,361,803 | 1/1968 | Augustynowicz | 562/417 |
| 3,970,696 | 7/1976 | Shigeyasu | 562/416 |

Primary Examiner—A. Siegel
Attorney, Agent, or Firm—Frishauf, Holtz, Goodman & Woodward

[57] ABSTRACT

An improved process for the production of a high purity terephthalic acid by a liquid phase oxidation reaction of para-xylene by means of molecular oxygen or a molecular oxygen-containing gas in an aliphatic monocarboxylic acid solvent in the presence of a cobalt-manganese-bromine catalyst system, characterized in that as the cobalt-manganese-bromine catalyst system there is used a catalyst system of a specific composition at a specific concentration, and the liquid phase oxidation reaction is effected in the presence of acetaldehyde in addition to the cobalt-manganese-bromine catalyst system under relatively mild temperature (170°–190° C.) and pressure conditions while maintaining the water concentration in the reaction system at a specified low level. The terephthalic acid produced according to the process of the present invention is of so high a quality that it can be used for the direct production of a polyalkylene terephthalate from the acid and an alkylene glycol or ethylene oxide, which direct production does not need the preparation of an intermediate such as a methyl ester of terephthalic acid.

18 Claims, No Drawings

PROCESS FOR THE PRODUCTION OF A HIGH PURITY TEREPHTHALIC ACID

This invention relates to a process for the production of terephthalic acid. More particularly, this invention relates to a process according to which a high purity terephthalic acid that can be directly used for the manufacture of a polyalkylene terephthalate is produced by a liquid phase oxidation reaction of para-xylene with industrial advantages.

As one of the processes for preparing terephthalic acid from para-xylene, the so-called Scientific Design method (SD method) is known and disclosed in Japanese Patent Publication No. 2666/1959. According to this known method, para-xylene is oxidized by means of molecular oxygen in the liquid phase comprising a lower aliphatic carboxylic acid as a reaction solvent in the presence of a catalyst comprising bromine and a heavy metal or heavy metals such as cobalt and/or manganese. The terephthalic acid obtained according to this method still contains large amounts of intermediates such as 4-carboxybenzaldehyde and para-toluic acid and other impurities, and the crystals precipitated by crystallization of the product are yellow. Therefore, the crude terephthalic acid product prepared according to this known method cannot be directly used for the manufacture of a polyalkylene terephthalate. Various methods have heretofore been proposed for the purification of such crude terephthalic acid containing large amounts of impurities, but any of these purification methods is not industrially advantageous because expensive equipment is necessary and/or complicated steps are needed. Accordingly, for the production of polyethylene terephthalate, there has been inevitably adopted a process in which such crude terephthalic acid is first esterified with methanol to form dimethyl terephthalate that is easy to purify by distillation and the dimethyl terephthalate is then subjected to ester-exchange with ethylene glycol, followed by polycondensation.

In the process wherein terephthalic acid is prepared by the liquid phase oxidation of para-xylene, oxidation to toluic acid as an intermediate proceeds relatively with ease but in general, oxidation of the toluic acid to terephthalic acid is very difficult because of the influence of the substituent(—COOH). Since the SD method was disclosed, there have been proposed various improved processes for promoting this oxidation. For example, there are mentioned a process in which a very large amount of a cobalt catalyst is used (see Japanese Patent Publication No. 11650/1969), and various processes in which a reaction promotor is used, e.g., a process in which an inorganic bromine compound is used as a reaction promotor in association with a cobalt catalyst (see Japanese Patent Publication No. 36732/1970), a process in which an organic bromine compound is used as a reaction promotor (see Japanese Patent Application Laid-Open Specifications No. 135940/1974 and No. 43734/1976), and a process in which an alkali metal atom is used in association with a cobalt-manganese-bromine catalyst system (see Japanese Patent Application Laid-Open Specification No. 70741/1976). These processes are excellent from the viewpoint of high purity of the terephthalic acid produced thereby. However, each of these processes is still disadvantageous from other points of view. For example, depending on the process, an expensive starting material such as an organic bromine compound must be used, a step for preventing accumulation of metal ions is needed, and/or the concentration of 4-carboxybenzaldehyde (hereinafter often referred to as "4-CBA") in terephthalic acid crystals is caused to be as high as several hundred ppm. Further, in any of these processes, reduction of the concentrations of impurities such as 4-CBA is still insufficient. In addition, these processes with the purpose of improving the catalyst activity are defective in that combustion of acetic acid as the solvent, which is an undesirable side reaction, is promoted, resulting in the economical disadvantage when the production of terephthalic acid is practiced on an industrial scale. It is said that in the case of direct polymerization for the production of a special polyester film such as one for the manufacture of magnetic tapes as used in computers, terephthalic acid must be so pure that the 4-CBA concentration contained therein is as low as less than 100 ppm. Accordingly, it has been strongly desired to further reduce the 4-CBA concentration and simultaneously hold down the combustion of acetic acid.

We previously found that when the liquid phase oxidation of para-xylene is carried out in the presence of a cobalt-manganese-hydrogen bromide catalyst system having a composition within a specific range while maintaining the water content in the reaction system at 3 to 9% by weight based on the solvent, a high purity terephthalic acid having a very low concentration of impurities such as 4-CBA can be obtained with a much reduced combustion of the solvent such as acetic acid. We further made our researches and found that when the liquid phase oxidation of para-xylene is carried out in the presence of the above-mentioned catalyst system while controlling the water concentration of the reaction system within the range of 3 to 9% by weight based on the solvent, if at least one oxidizable compound selected from the group consisting of specific aliphatic alcohols, specific aliphatic aldehydes and specific aliphatic ketones is further present as a promoting additive in the reaction system in association with the catalyst, terephthalic acid having a further improved purity can be obtained.

In the production, by the liquid phase oxidation, of terephthalic acid for the direct production of a polyalkylene terephthalate, the reduction of the combustion loss of an aliphatic monocarboxylic acid solvent due to oxidation in addition to the improvement of the quality of terephthalic acid is a very important technical aspect to be taken into consideration for economizing the process for the production of terephthalic acid.

In order to heighten the purity of terephthalic acid, the oxidizability of para-xylene is generally improved, for example, by elevating the reaction temperature and/or an oxygen partial pressure or by employing a highly active catalyst. However, by adoption of such means, combustion or decomposition of the aliphatic monocarboxylic acid solvent is simultaneously accelerated. This is a serious defect inevitably involved in the conventional processes for the production of terephthalic acid by the liquid phase oxidation of para-xylene.

It is a principal object of this invention to provide an improved process, according to which a high purity terephthalic acid from which a fiber grade polyethylene terephthalate can be directly obtained by the esterification reaction with ethylene glycol or ethylene oxide to form bis-(β-hydroxyethyl) terephthalate and the subsequent polycondensation thereof, can be produced with industrial advantages by the liquid phase oxidation of para-xylene.

Another object of this invention is to provide a process for the production of terephthalic acid by the liquid phase oxidation of para-xylene, according to which the combustion loss of an aliphatic monocarboxylic acid solvent due to oxidation can be reduced while the quality of terephthalic acid crystals is maintained at so high a level that the terephthalic acid can advantageously be employed for the direct production of a polyethylene terephthalate.

Other and further objects of this invention will become obvious upon an understanding of the illustrative embodiments about to be described or will be indicated in the appended claims, and various advantages not referred to herein will occur to one skilled in the art upon employment of the invention in practice.

With a view to reducing the combustion loss of the reaction solvent due to oxxidation with maintaining the quality of terephthalic acid crystals at a high level, we made intensive searches for the process for the production of a high purity terephthalic acid useful for direct esterification and polycondensation in which process the liquid phase oxidation of para-xylene is effected in an aliphatic monocarboxylic acid solvent in the presence of the aforementioned promoting additive in association with a cobalt-mangasese-bromine catalyst system while maintaining the water content in the reaction system at 3 to 9% by weight based on the solvent. As a result, it was surprisingly found that the combustion loss of the solvent can be remarkably diminished by considerably lowering the reaction temperature, and if the afformentioned promoting additive is present in the reaction system, the oxidizability of para-xylene which is reduced by the lowering of the reaction temperature can be remarkably restored to a high level without substantial increase of decomposition or combustion of the solvent. It was also found that though any of the aforementioned promoting additives exerts more or less a promoting effect, acetaldehyde exerts, among others, an especially excellent effect even if it is used in a small amount and by the use of acetaldehyde, terephthalic acid having a much improved quality can be obtained with a much reduced combustion loss of the solvent. Based on these findings, we have now completed the present invention.

More specifically, according to this invention, there is provided a process for the production of a high purity terephthalic acid by a liquid phase oxidation reaction of para-xylene by means of molecular oxygen or a molecular oxygen-containing gas in an aliphatic monocarboxylic acid solvent in the presence of a cobalt-manganese-bromine catalyst system, characterized in that in the liquid phase oxidation reaction, there is used acetaldehyde in an amount of 0.05 to 0.60 mole per mole of para-xylene and as the cobalt-manganese-bromine catalyst system (A) at least one cobalt compound selected from the group consisting of cobalt acetate, cobalt propionate, cobalt butyrate, cobalt naphthenate, cobalt carbonate, cobalt benzoate, cobalt bromoacetate, cobalt bromide and hydrates thereof, (B) at least one manganese compound selected from the group consisting of manganese acetate, manganese propionate, manganese butyrate, manganese naphthenate, manganese carbonate, manganese benzoate, manganese bromacetate, manganese bromide and hydrates thereof and (C) at least one bromine compound selected from the group consisting of hydrogen bromide, cobalt bromide and hydrates thereof, manganese bromide and hydrates thereof, bromoacetic acid, cobalt bromoacetate and a hydrate thereof, manganese bromoacetate and a hydrate thereof, aralkyl bromides and alkane bromides, in amount such as will provide a cobalt atom concentration of 0.01 to 0.05% by weight based on the aliphatic monocarboxylic acid solvent, a manganese atom concentration of 35 to 100% by weight based on the cobalt atom and a bromine atom concentration of 0.10 to 0.40% by weight based on the aliphatic monocarboxylic acid solvent, and the liquid phase oxidation reaction is effected at a temperature of 170° to 190° C. under an elevated pressure while maintaining the water concentration in the reaction system at a level of 3 to 9% by weight based on the aliphatic monocarboxylic acid, followed by separation and recovery of terephthalic acid crystals from the reaction mixture.

According to this invention, a high purity terephthalic acid useful for the direct esterification and polycondensation can be obtained while controlling the loss of the solvent due to decomposition or combustion at a very low level.

This invention will now be described in detail.

The process of this invention for the production of terephthalic acid by the liquid phase oxidation of para-xylene in an aliphatic monocarboxylic acid solvent in the presence of a cobalt-manganese-bromine catalyst system having a specific composition at a specific water concentration in the reaction mixture, is characterized in that the liquid phase oxidation is effected at a specific low reaction temperature in the presence of acetaldehyde as a co-oxidizable agent.

Lower aliphatic monocarboxylic acids such as acetic acid, propionic acid and butyric acid are preferred as a solvent, and, of them, acetic acid is most preferred. For simplification of the illustration, this invention will be described hereinafter mainly by reference to embodiments in which acetic acid is used as the solvent. Of course, it should be noted that the process of this invention can also be practiced by the use of aliphatic monocarboxylic acids other than acetic acid or mixtures of aliphatic monocarboxylic acids.

Acetaldehyde is used as a co-oxidizable additive in practicing the process of this invention. It is conceivable to use other additives, such as aliphatic alcohols having 1 to 3 carbon atoms, e.g., methanol, ethanol and propanols, aliphatic aldehydes having 1 to 3 carbon atoms, other than acetaldehyde, e.g., formaldehyde and propionaldehyde, paraldehyde, and aliphatic ketones having 3 to 5 carbon atoms, e.g., acetone, methyl ethyl ketone and diethyl ketone. But, for example, with the use of acetone, methyl ethyl ketone, diethyl ketone etc., an effect as will be attained in this invention is insufficient and the quality of the resulting terephthalic acid is unsatisfactory. In this sense, acetaldehyde has a peculiar and marked effect under the above-mentioned oxidation conditions. This peculiar effect cannnot be attained by the use of any of the above-mentioned promoting additives. This invention is based on the discovery of this peculiar effect attained by the use of acetaldehyde. Even in the case of paraldehyde, a trimer of acetaldehyde, which promptly decomposes in an oxidation system to produce acetaldehyde and which is therefore expected to exert the same effect as that of acetaldehyde, the effect as will be attained by the use of acetaldehyde in this invention is not recognized. Contrary to our expectation, under some oxidation conditions, paraldehyde exerts even an oxidation-inhibiting effect.

When an oxidizable substance such as paraldehyde other than acetaldehyde is incorporated in an amount of 10 mole % based on para-xylene and the oxidation is effected at a water concentration of 7% by weight based on the acetic acid solvent under such relatively violent oxidation conditions that the temperature is 196° C., there is obtained substantially the same effect with respect to the quality of terephthalic acid as in the case of the use of acetaldehyde in an amount of 10 mole % based on paraxylene, but under such relatively mild oxidation conditions that the temperature is 190° C. or less, the difference in the effect attained with respect to the quality of terephthalic acid becomes conspicuous between the case of the use of acetaldehyde and that of other oxidizable substances as the additive. The reason why such a difference is caused has not yet been elucidated in detail, but it is believed that the above difference may probably be due to the differences in the oxidizability of the promoting additive and in the kind of complex formed thereof with catalytic metal compounds.

Acetaldehyde is added in an amount of 0.05 to 0.6 mole and preferably 0.10 to 0.30 mole per mole of para-xylene charged. When the amount of acetaldehyde is smaller than 0.05 mole per mole of para-xylene, no substantial effect can be attained. When acetaldehyde is added in an amount of 0.10 to 0.6 mole per mole of para-xylene, especially advantageous results can be obtained from the economical viewpoint. The intended effect increases as the amount of acetaldehyde is increased, but when the amount of acetaldehyde is larger than 0.6 mole per mole of para-xylene, generation of heat by oxidation of acetaldehyde cannot be neglected any more and it is very difficult to operate the oxidation while keeping the reaction temperature mild. As is well-known, the difficulty of removal of the reaction heat becomes serious as the reaction vessel is enlarged in dimensions so as to increase the productivity. Further, when acetaldehyde is added in too large an amount, even if a high quality terephthalic acid can be obtained with a low combustion ratio of the solvent, the cost of acetaldehyde used is increased and the unit consumption of the additive, expressed in terms of the ratio of the cost of acetaldehyde to the weight of terephthalic acid formed, is increased. Therefore, needless to say, the amount of acetaldehyde is also restricted from this point of view.

When the oxidation reaction is carried out batchwise, the predetermined amount of acetaldehyde may be charged into a reaction vessel in advance. When the oxidation is continuously effected, a solution of acetaldehyde in acetic acid and/or para-xylene may be continuously fed into a reaction vessel through a starting material feed line or a reflux line for the condensate of an off-gas discharged from the top of the reaction vessel. Acetaldehyde thus added is partially oxidized during the reaction, and it is believed that acetaldehyde itself, intermediates and oxidation products act on the catalyst to selectively enhance the oxidizability of para-xylene while holding down the combustion of the solvent. The oxidation products of acetaldehyde are finally converted into various acids such as formic acid and acetic acid, methyl acetate, water, carbon dioxide and carbon monoxide, and hence they are not left in the product in the form of impurities. The formed acids serve for compensating the loss of acetic acid which undergoes combustion slightly under the oxidation conditions as adopted in this invention. In this connection, the process of this invention is advantageous in that the conversion of acetaldehyde into acetic acid is selectively high as compared with those into other oxidation products.

Acetaldehyde is nowadays used as an important starting material as well as carbon monoxide and methanol in the Monsanto process for the manufacture of acetic acid. According to this invention, the loss of acetic acid due to combustion can be compensated by cheaper acetaldehyde, and hence the unit of the loss of acetic acid due to combustion can be substantially reduced by the use of acetaldehyde. This is one of economical advantages attained by this invention.

In the process of this invention, it is preferred that the concentration of para-xylene in the aliphatic monocarboxylic acid solution to be fed into the oxidation reaction system be 12 to 25% by weight.

In the process of this invention, it is undispensable that the reaction temperature should be maintained at a relatively low level as compared with the temperatures adopted in the conventional oxidation processes in which a cobalt-manganese-bromine catalyst system is used, namely it should be maintained at a level of 170° to 190° C., and a preferred reaction temperature is in the range of from 175° to 185° C. When the reaction temperature is lower than 170° C., a high purity terephthalic acid having a less degree of coloring and a low concentration of impurities such as 4-CBA cannot be obtained unless acetaldehyde is added in too large an amount in disregard of economical conditions. At a reaction temperature higher than 190° C., the combustion loss of acetic acid is drastically increased, and therefore, the adoption of such a high reaction temperature is not preferred from the economical viewpoint as described hereinbefore.

In practicing the process of this invention, it is preferred to control the oxygen concentration in an off-gas to be discharged from the reaction vessel at a level of 3 to 8% by volume. If the oxygen concentration in the off-gas is more than 8% by volume, there is a fear of explosion.

In the process of this invention, since the oxidation is carried out at a relatively low temperature, the vapor pressure of the solvent in the reaction vessel is inevitably low. In order to effectively remove the reaction heat by air supplied for oxidation, a low reaction pressure is preferred. This is so because the vaporization of the solvent etc. is enhanced at a low pressure and hence the latent heat of vaporization becomes large. In the process of this invention, it is possible to carry out the oxidation at a reaction pressure of 5 to 20 kg/cm$^2$G, preferably 8 to 15 kg/cm$^2$G, which is much lower than the reaction pressure as adopted in the conventional oxidation processes. Since the oxidation is carried out under such mild temperature and pressure conditions, levels of performance required of the reaction vessel, such as corrosion resistance against water-containing acetic acid and hydrogen bromide and pressure resistance, are caused to lower. Accordingly, the manufacturing cost of the reaction vessel can be lowered. This is also one of economical advantages attained by this invention.

Air is advantageously used as the molecular oxygen-containing gas from the industrial point of view.

The cobalt and manganese catalytic compounds are used in the form of an acid solvent-soluble salt such as an acetate, a propionate, a butyrate, a naphthenate, a bromoacetate or a benzoate. Alternatively, they may be used in the form of a salt that can be decomposed and solubilized by the acid, such as a carbonate, or in the form of a salt with bromine or bromoacetate, namely the other catalyst source, so far as the intended composition of the catalyst system can be obtained in the reaction system. These salts may be either anhydrous salts or hydrates, but hydrates are easily available in general. These cobalt and manganese salts may be either bivalent metal salts or trivalent metal salts, but bivalent metal salts are preferred because they are stable and inexpensive.

The cobalt salt is used in such an amount as will provide a cobalt atom concentration of 0.01 to 0.05% by weight and preferably 0.03 to 0.05% by weight based on the solvent. The manganese salt is used in such an amount as will provide a manganese atom concentration of 35 to 100% by weight, preferably 35 to 70% based on the cobalt atom.

In the process of this invention, it is preferred that the source of bromine be added in the form of hydrogen bromide, but a part or all of the bromine source may be added in the form of cobalt bromide, manganese bromide, cobalt bromoacetate or manganese bromoacetate. The addition of the bromine source may be effected in either manner as described above so far as the intended composition of the catalyst system can be obtained. Alternatively, an aralkyl bromide, an alkane bromide or bromoacetic acid may be added as the bromine source compound. As the aralkyl bromide, there can be mentioned, for example, benzyl bromide, p-methylbenzyl bromide and ω-teterabromo-p-xylene

Of them, benzyl bromide and p-methylbenzyl bromide are more preferred. As the alkane bromide, there can be mentioned, for example, those having 1 to 4 carbon atoms and 1 to 4 bromine atoms. Specific examples of alkane bromides include methyl bromide, ethyl bromide, propyl bromides, dibromoethanes and tetrabromoethanes. The bromine compound is added in such an amount as will provide a bromine atom concentration of 0.10 to 0.40% by weight based on the solvent. It is preferred that the bromine compound be added in such an amount as will provide a bromine atom concentration of 0.12 to 0.2% by weight based on the solvent and the amount of the bromine atom be 270 to 540% by weight based on the cobalt atom. Of course, the above-mentioned cobalt compounds, the above-mentioned manganese compounds and the above-mentioned bromine compounds may be used alone or in combination as the respective catalyst sources.

In the process of this invention, it is indispensable that the water concentration in the reaction system should be maintained at a level of 3 to 9% by weight based on an aliphatic monocarboxylic acid solvent during the oxidation reaction, and it is preferred that the water concentration be maintained at a level of 5 to 7% by weight. When the water concentration exceeds 9% by weight, as illustrated in Examples given hereinafter, the content of 4-carboxybenzaldehyde as a main impurity is increased in the resulting terephthalic acid and the degree of coloring becomes high. On the other hand, it is economically disadvantageous to maintain the water concentration at a low level of less than 3% by weight during the oxidation. In addition, when the concentration of water having a large latent heat of vaporization is less than 3% by weight, the removal of the reaction heat tends to become difficult. It is noted that the maintenance of the above-specified water concentration exerts a specific synergistic effect together with the use of a specific small amount of a cobalt-manganese-bromine catalyst system, the use of a specific amount of acetaldehyde and the adoption of the above-mentioned specific oxidation conditions. The water concentration can be easily maintained at the above-specified level according to a known process in which an off-gas from the reaction vessel is cooled to condense entrained water and the amount of water to be returned to the reaction vessel is controlled.

In this invention, the mode of the process is not particularly critical, but it is preferred that the process be effected continuously. In case the process is continuously effected, it is preferred that the average residence time of the reaction mixture in the oxidation reaction system be 0.5 to 2.5 hours. Separation and recovery of terephthalic acid may be conducted according to the ordinary method in which the reaction mixture is withdrawn from the reaction system and gradually cooled to effect crystallization of terephthalic acid, followed by filtration or centrifugal separation. The recovered crystals are washed with acetic acid. The mother liquor is recycled to the reaction system and reused as a solvent.

As will be apparent from the foregoing illustration, according to this invention, by the use of acetaldehyde as a promoting additive in addition to a cobalt-manganese-bromine catalyst system, a high purity terephthalic acid useful for the direct esterification and polycondensation can be economically produced with a much reduced combustion loss of a solvent under industrially advantageous low temperature and low pressure conditions.

This invention will now be described in detail by reference to the following Examples that by no means limit the scope of the invention.

In Examples, the degree of coloring of terephthalic acid crystals was evaluated according to the Hazen number expressed in the APHA unit, which was determined in the following manner.

In 200 cc of concentrated hydrochloric acid (hydrogen chloride content: 35% by weight) were dissolved 2.499 g of potassium chloroplatinate ($K_2PtCl_3$) and 2.00 g of crystalline cobalt chloride ($CoCl_2 \cdot 6H_2O$), and the solution was diluted with distilled water to 1 liter to prepare a Hazen platinum-cobalt standard solution. The Hazen number of a solution obtained by diluting 1 cc of the standard solution with distilled water to a total volume of 1 liter was defined as 1 APHA and the Hazen number of a solution obtained by diluting X cc of the standard solution with distilled water to a total volume of 1 liter was defined as X APHA. A solution of 6 g of terephthalic acid crystals to be tested, dissolved in 120 cc of dimethylformamide, was prepared, and 100 cc of the solution was sampled into a color comparison tube. The color of the solution was compared with colors of several standard solutions of fixed APHA units filled in the same color comparison tubes in an amount of 100 cc, respectively, with naked eyes from above while placing these color comparison tubes on white paper. The APHA unit of the sample solution was thus determined.

The amount of acetic acid subjected to combustion was determined in the following manner.

The amounts of combustion products of acetic acid, namely carbon dioxide, carbon monoxide, methane, formic acid, formaldehyde and methyl acetate, were determined with respect to both of the off-gas and the mother liquor, and it was confirmed that the majority of the combustion products was carbon dioxide. The amount of acetic acid subjected to combustion was expressed in terms of ½ ×(the amount of carbon dioxide formed).

The content of 4-carboxybenzaldehyde in the terephthalic acid crystals was determined using Digital Polarograph PE-21 (tradename of a product manufactured by Yanagimoto Mfg. Co., Ltd., Japan) (half wave potential: −1.24 volts).

The water concentration in the reaction system was determined using Karl Fischer Moisture Content Meter NK-SS (tradename of a product manufactured and sold by Kyoto Electronics Manufacturing Co., Ltd., Japan).

The cobalt and manganese atom concentrations in the reaction system were determined using Atomic-Absorption/Spectrophotometer Model 170-10 (tradename of a product manufactured by Hitachi Ltd., Japan).

The bromine atom concentration in the reaction system was determined using X-Ray Spectrometer KG-3 (tradename of a product manufactured and sold by Rigaku Corp., Japan).

EXAMPLE 1

A titanium pressure-resistant reaction vessel having an internal capacity of 80 liters and equipped with a reflux condenser, a stirrer, a heating device, a starting material feed inlet, a gas feed inlet, a slurry discharge outlet, a slurry withdrawal device connected with the slurry discharge outlet, and a titanium-made crystallizing vessel having an internal capacity of 50 liters and provided with a cooler was charged with 30 kg of acetic acid, 50.7 g of cobalt(II) acetate (tetrahydrate) (the cobalt atom concentration: 0.04% by weight based on acetic acid), 21.4 g of manganese(II) acetate (tetrahydrate) (the manganese atom concentration: 40% by weight based on the cobalt atom), 8.4 g of hydrobromic acid (47% aqueous solution) (the bromine atom concentration: 0.13% by weight based on acetic acid) and 2.10 kg of water (7.0% by weight based on acetic acid). Air was continuously introduced into the reaction vessel from the bottom thereof so that the oxygen concentration in the off-gas was 5 to 8% by volume. Under such reaction conditions that the temperature is 182° C. and the pressure is 10 kg/cm$^2$G, an acetic acid solution containing 17% by weight, based on acetic acid, of para-xylene and 1.8% by weight, based on acetic acid, of acetaldehyde (0.25 mole % based on para-xylene) was continuously introduced into the reaction vessel so that the average residence time was 2 hours. The catalyst source compounds were intermittently supplied during the oxidation reaction so that the initial concentration of the catalyst system was maintained. The reaction mixture slurry was continuously withdrawn into the crystallizing vessel by means of the slurry withdrawal device and was cooled to about 110° C. in the crystallizing vessel. Then, the mother liquor was separated by means of a centrifugal separator and removed. The recovered terephthalic acid was washed with acetic acid in an amount three times by volume the amount of the terephthalic acid at a still high temperature (80° C.) and then washed with water in an amount three times by volume the amount of the terephthalic acid, followed by filtration and drying. When the operation became completely stable (about 10 hours after the start of the operation), the quality of the terephthalic acid and the concentration of impurities were determined to obtain the results shown in Table 1.

EXAMPLES 2 TO 11 AND COMPARATIVE EXAMPLES 1 TO 11

The continuous oxidation of para-xylene was carried out in the same manner as described in Example 1 except that the reaction temperature and the concentrations of Co, Mn, Br and water were changed as indicated in Table 1 and 2, and the subsequent post treatments were conducted in the same manner as described in Example 1. The obtained results are shown in Tables 1 and 2.

From the results as shown in Tables 1 and 2, it is apparent that the goods results were obtained when the water concentration, the cobalt atom concentration, the manganese atom concentration, the bromine atom concentration and the reaction temperature were each in the range as specified in this invention.

TABLE 1

| Example No. | Temperature (°C.) | Co Concentration (% by weight based on acetic acid) | Mn Concentration (% by weight based on Co) | Br Concentration (% by weight based on acetic acid) | Water Concentration (% by weight based on acetic acid) | Content (ppm) of 4-Carboxybenzaldehyde | Hazen number (APHA) | Amount of Acetic Acid Subjected to Combustion (mole per mole of para-xylene |
|---|---|---|---|---|---|---|---|---|
| 1 | 182 | 0.04 | 40 | 0.13 | 7.0 | 210 | 5 | 0.17 |
| 2 | 182 | 0.02 | 45 | 0.15 | 6.0 | 230 | 6 | 0.14 |
| 3 | 182 | 0.01 | 50 | 0.14 | 4.5 | 265 | 8 | 0.10 |
| 4 | 182 | 0.04 | 65 | 0.12 | 6.8 | 205 | 5 | 0.18 |
| 5 | 176 | 0.05 | 38 | 0.14 | 5.3 | 240 | 6 | 0.16 |
| 6 | 185 | 0.02 | 40 | 0.12 | 5.7 | 220 | 5 | 0.14 |
| 7 | 182 | 0.04 | 40 | 0.13 | 5.0 | 210 | 5 | 0.18 |
| 8 | 182 | 0.04 | 40 | 0.13 | 8.0 | 215 | 5 | 0.17 |
| 9 | 182 | 0.02 | 45 | 0.12 | 6.3 | 240 | 6 | 0.12 |
| 10 | 182 | 0.02 | 45 | 0.19 | 5.9 | 225 | 6 | 0.16 |
| 11 | 182 | 0.02 | 45 | 0.30 | 6.3 | 225 | 8 | 0.21 |

TABLE 2

| Comparative Example No. | Temperature (°C.) | Co Concentration (% by weight based on acetic acid) | Mn Concentration (% by weight based on Co) | Br Concentration (% by weight based on acetic acid) | Water Concentration (% by weight based on acetic acid) | Results of Analysis | | Amount of Acetic Acid Subjected to Combustion (mole per mole of para-xylene) |
|---|---|---|---|---|---|---|---|---|
| | | | | | | Content (ppm) of 4-Carboxybenzaldehyde | Hazen number (APHA) | |
| 1 | 182 | 0.005 | 35 | 0.10 | 8.0 | 390 | 18 | 0.08 |
| 2 | 182 | 0.04 | 10 | 0.13 | 7.5 | 520 | 14 | 0.12 |
| 3 | 182 | 0.03 | 20 | 0.14 | 7.2 | 330 | 10 | 0.16 |
| 4 | 183 | 0.08 | 40 | 0.15 | 5.5 | 210 | 4 | 0.35 |
| 5 | 181 | 0.10 | 35 | 0.17 | 5.8 | 200 | 5 | 0.43 |
| 6 | 182 | 0.03 | 33 | 0.09 | 7.3 | 320 | 11 | 0.13 |
| 7 | 165 | 0.05 | 40 | 0.15 | 6.4 | 340 | 9 | 0.12 |
| 8 | 198 | 0.05 | 35 | 0.14 | 5.3 | 200 | 5 | 0.31 |
| 9 | 182 | 0.04 | 40 | 0.13 | 9.5 | 350 | 8 | 0.15 |
| 10 | 182 | 0.04 | 40 | 0.13 | 10.7 | 490 | 12 | 0.10 |
| 11 | 182 | 0.02 | 45 | 0.07 | 6.1 | 410 | 8 | 0.09 |

EXAMPLES 12 TO 14 AND COMPARATIVE EXAMPLES 12 TO 17

The continuous oxidation of para-xylene was carried out in the same manner as described in Example 1 except that the kind and amount of the additive used were changed as shown in Table 3, and the post treatments were conducted in the same manner as described in Example 1. The obtained results are shown in Table 3.

TABLE 3

| | Additive | | Results of Analysis | |
|---|---|---|---|---|
| | Kind | Amount (mole per mole of para-xylene) | Content (ppm) of 4-Carboxybenzaldehyde | Hazen Number (APHA) |
| Example 12 | Acetaldehyde | 0.05 | 230 | 5 |
| Example 13 | Acetaldehyde | 0.15 | 220 | 5 |
| Example 14 | Acetaldehyde | 0.40 | 200 | 4 |
| Comparative Example 12 | Methyl ethyl ketone | 0.25 | 2125 | 16 |
| Comparative Example 13 | Acetone | 0.25 | 330 | 10 |
| Comparative Example 14 | Paraldehyde | 0.25 | 2535 | 12 |
| Comparative Example 15 | Methanol | 0.25 | 310 | 7 |
| Comparative Example 16 | Acetaldehyde | 0.01 | 260 | 6 |
| Comparative | Not | — | 240 | 8 |
| Example 17 | added Acetaldehyde | 0.25 | 210 | 5 |

EXAMPLES 15 TO 29

The continuous oxidation of para-xylene was carried out in the same manner as described in Example 1 except that the kinds of the cobalt, manganese and bromine compounds used and the water concentration in the reaction system were changed as indicated in Table 4, and the post treatments were conducted in the same manner as described in Example 1. The cobalt, manganese and bromine compounds were used in such amounts that the cobalt, manganese and bromine atom concentrations were the same as those in Example 1. Accordingly, in case the compound or compounds containing a bromine atom and either a cobalt atom or a manganese atom were used as the cobalt compound and/or the manganese compound (Examples 22, 24, 26 and 27), the compound or compounds were used in such an amount or amounts that the cobalt and/or manganese atom concentration was the same as that or those in Example 1, and hydrogen bromide or bromoacetic acid was used in such an amount that the total bromine atom concentration was the same as that in Example 1.

TABLE 4

| Example No. | Cobalt Compound | Manganese Compound | Bromine Compound |
|---|---|---|---|
| 15 | Cobalt (II) acetate (tetrahydrate) | Manganese (II) acetate (tetrahydrate) | Benzyl bromide |
| 16 | Cobalt (II) acetate (anhydrous) | Manganese (II) acetate (anhydrous) | 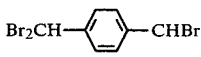 |
| 17 | Cobalt (II) acetate (tetrahydrate) | Manganese (II) acetate (tetrahydrate) | Monobromoethane |
| 18 | Cobalt (II) acetate (tetrahydrate) | Manganese (II) acetate (tetrahydrate) | Bromoacetic acid |
| 19 | Cobalt (II) propionate (trihydrate) | Manganese (II) propionate (trihydrate) | Hydrogen bromide |
| 20 | Cobalt (II) carbonate (hexahydrate) | Manganese (II) carbonate (monohydrate) | Hydrogen bromide |
| 21 | Cobalt (II) | Manganese (II) | |

TABLE 4-continued

| | | | |
|---|---|---|---|
| | benzoate (anhydrous) | benzoate (tetrahydrate) | Hydrogen bromide |
| 22 | Cobalt (II) bromoacetate (anhydrous) | Manganese (II) bromoacetate (anhydrous) | Bromoacetic acid |
| 23 | Cobalt (II) butyrate (anhydrous) | Manganese (II) butyrate (dihydrate) | Hydrogen bromide |
| 24 | Cobalt (II) carbonate (basic) | Manganese (II) bromoacetate (anhydrous) | Hydrogen bromide |
| 25 | Cobalt (II) carbonate (hexahydrate) | Manganese (II) carbonate (monohydrate) | Bromoacetic acid |
| 26 | Cobalt (II) bromide (hexahydrate) | Manganese (II) bromide (tetrahydrate) | Hydrogen bromide |
| 27 | Cobalt (II) bromide (anhydrous) | Manganese (II) bromide (anhydrous) | Hydrogen bromide |
| 28 | Cobalt (II) naphthenate | Manganese (II) naphthenate | Benzyl bromide |
| 29 | Cobalt (II) naphthenate | Manganese (II) naphthenate | Hydrogen bromide |

Results of Analysis

| Example No. | Water Concentration (% by weight based on acetic acid) | Content (ppm) of 4-Carboxy-benzaldehyde | Hazen Number (APHA) | Amount of Acetic Acid Subjected to Combustion (mole per mole of para-xylene) |
|---|---|---|---|---|
| 15 | 3.4 | 220 | 6 | 0.16 |
| 16 | 4.7 | 230 | 7 | 0.15 |
| 17 | 4.8 | 225 | 5 | 0.14 |
| 18 | 7.2 | 220 | 6 | 0.15 |
| 19 | 5.3 | 205 | 5 | 0.16 |
| 20 | 7.6 | 210 | 5 | 0.17 |
| 21 | 6.1 | 225 | 7 | 0.18 |
| 22 | 7.4 | 225 | 6 | 0.15 |
| 23 | 5.7 | 210 | 5 | 0.18 |
| 24 | 5.8 | 215 | 6 | 0.16 |
| 25 | 8.2 | 225 | 7 | 0.17 |
| 26 | 7.5 | 210 | 5 | 0.17 |
| 27 | 7.9 | 210 | 6 | 0.17 |
| 28 | 6.7 | 225 | 5 | 0.18 |
| 29 | 6.8 | 215 | 6 | 0.18 |

What we claim is:

1. In a process for the production of a high purity terephthalic acid by a liquid phase oxidation reaction of para-xylene by means of molecular oxygen or a molecular oxygen-containing gas in an aliphatic monocarboxylic acid solvent in the presence of a cobalt-manganese-bromine catalyst system, the improvement wherein in the liquid phase oxidation reaction, there are used acetaldehyde in an amount of 0.05 to 0.60 mole per mole of para-xylene and as the cobalt-manganese-bromine catalyst system (A) at least one cobalt compound selected from the group consisting of cobalt acetate, cobalt propionate, cobalt butyrate, cobalt naphthenate, cobalt carbonate, cobalt benzoate, cobalt bromoacetate, cobalt bromide and hydrates thereof, (B) at least one manganese compound selected from the group consisting of manganese acetate, manganese propionate, manganese butyrate, manganese naphthenate, manganese carbonate, manganese benzoate, manganese bromoacetate, manganese bromide and hydrates thereof and (C) at least one bromine compound selected from the group consisting of hydrogen bromide, cobalt bromide and hydrates thereof, manganese bromide and hydrates thereof, bromoacetic acid, cobalt bromoacetate and a hydrate thereof, manganese bromoacetate and a hydrate thereof, aralkyl bromides and alkane bromides, in amount such as will provide a cobalt atom concentration of 0.01 to 0.05% by weight based on the aliphatic monocarboxylic acid solvent, a manganese atom concentration of 35 to 100% by weight based on the cobalt atom and a bromine atom concentration of 0.10 to 0.40% by weight based on the aliphatic monocarboxylic acid solvent, and the liquid phase oxidation reaction is effected at a temperature of 170° to 190° C. under an elevated pressure while maintaining the water concentration in the reaction system at a level of 3 to 9% by weight based on the aliphatic monocarboxylic acid, followed by separation and recovery of terephthalic acid crystals from the reaction mixture.

2. An improved process according to claim 1 wherein the aliphatic monocarboxylic acid solvent is acetic acid, propionic acid or butyric acid.

3. An improved process according to claim 1 wherein the molecular oxygen-containing gas is air.

4. An improved process according to claim 1 wherein the liquid phase oxidation reaction is carried out so that the oxygen concentration in an off-gas discharged from the reaction zone is 3 to 8% by volume.

5. An improved process according to claim 1 wherein the cobalt compound is cobalt(II) acetate or a hydrate thereof.

6. An improved process according to claim 1 wherein the cobalt atom concentration is 0.03 to 0.05% by weight based on the aliphatic monocarboxylic acid solvent.

7. An improved process according to claim 1 wherein the manganese compound is manganese(II) acetate or a hydrate thereof.

8. An improved process according to claim 1 wherein the manganese atom concentration is 35 to 70% by weight based on the cobalt atom.

9. An improved process according to claim 1 wherein the bromine atom concentration is 0.12 to 0.20% by weight based on the aliphatic monocarboxylic acid solvent.

10. An improved process according to claim 1 wherein the bromine compound is hydrogen bromide.

11. An improved process according to claim 1 wherein the bromine compound is an aralkyl bromide selected from benzyl bromide and p-methylbenzyl bromide.

12. An improved process according to claim 1 wherein acetaldehyde is used in an amount of 0.10 to 0.30 mole per mole of para-xylene.

13. An improved process according to claim 1 wherein the water concentration is maintained in the range of from 5 to 7% by weight based on the aliphatic monocarboxylic acid solvent.

14. An improved process according to claim 1 wherein the reaction temperature is 175° to 185° C.

15. An improved process according to claim 1 wherein the reaction process is 5 to 20 kg/cm$^2$G.

16. An improved process according to claim 15 wherein the reaction pressure is 8 to 15 kg/cm$^2$G.

17. An improved process according to claim 1 wherein the concentration of para-xylene in the aliphatic monocarboxylic acid solution to be fed into the oxidation reaction system is 12 to 25% by weight.

18. An improved process according to claim 1 wherein the average residence time of the reaction mixture in the oxidation reaction system is 0.5 to 2.5 hours in case the process is continuously effected.

* * * * *